United States Patent [19]

Schmadel, Jr.

[11] Patent Number: 4,725,137

[45] Date of Patent: Feb. 16, 1988

[54] PROCESS AND APPARATUS FOR MEASURING AND EVANESCENT FIELD IN AN OPTICAL FIBER

[75] Inventor: Donald C. Schmadel, Jr., Kensington, Md.

[73] Assignee: Chevron Research Company, San Francisco, Calif.

[21] Appl. No.: 546,611

[22] Filed: Oct. 28, 1983

[51] Int. Cl.⁴ .......................................... G01N 21/84
[52] U.S. Cl. .................................................. 356/73.1
[58] Field of Search ..................... 356/73.1; 350/96.15

[56] References Cited

U.S. PATENT DOCUMENTS 4,387,954 6/1983 Beasley ............................. 350/96.15
4,536,058 8/1985 Shaw et al. ..................... 356/73.1 X

FOREIGN PATENT DOCUMENTS 2840824 9/1979 Fed. Rep. of Germany ... 350/96.15
2492115 4/1982 France .............................. 350/96.15

Primary Examiner—Vincent P. McGraw
Attorney, Agent, or Firm—S. R. LaPaglia; E. J. Keeling; A. Stephen Zavell

[57] ABSTRACT

An apparatus and process are described which can measure the strength of an evanescent field at the surface of an optical fiber. Light is injected into an end of the optical fiber while the portion of the fiber to be tested is contacted with a material having a higher index of refraction than the optical fiber. The amount of light lost, i.e., coupled out of the fiber, is a function of the evanescent field strength at the cladding surface of the optical fiber. This loss can be correlated with optical fibers which have thicker and thinner claddings to determine the thickness of the cladding and/or the extent of removal of the cladding by, for example, etching.

18 Claims, 6 Drawing Figures

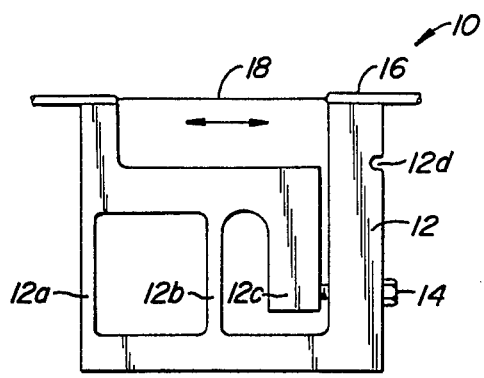
FIG._1.
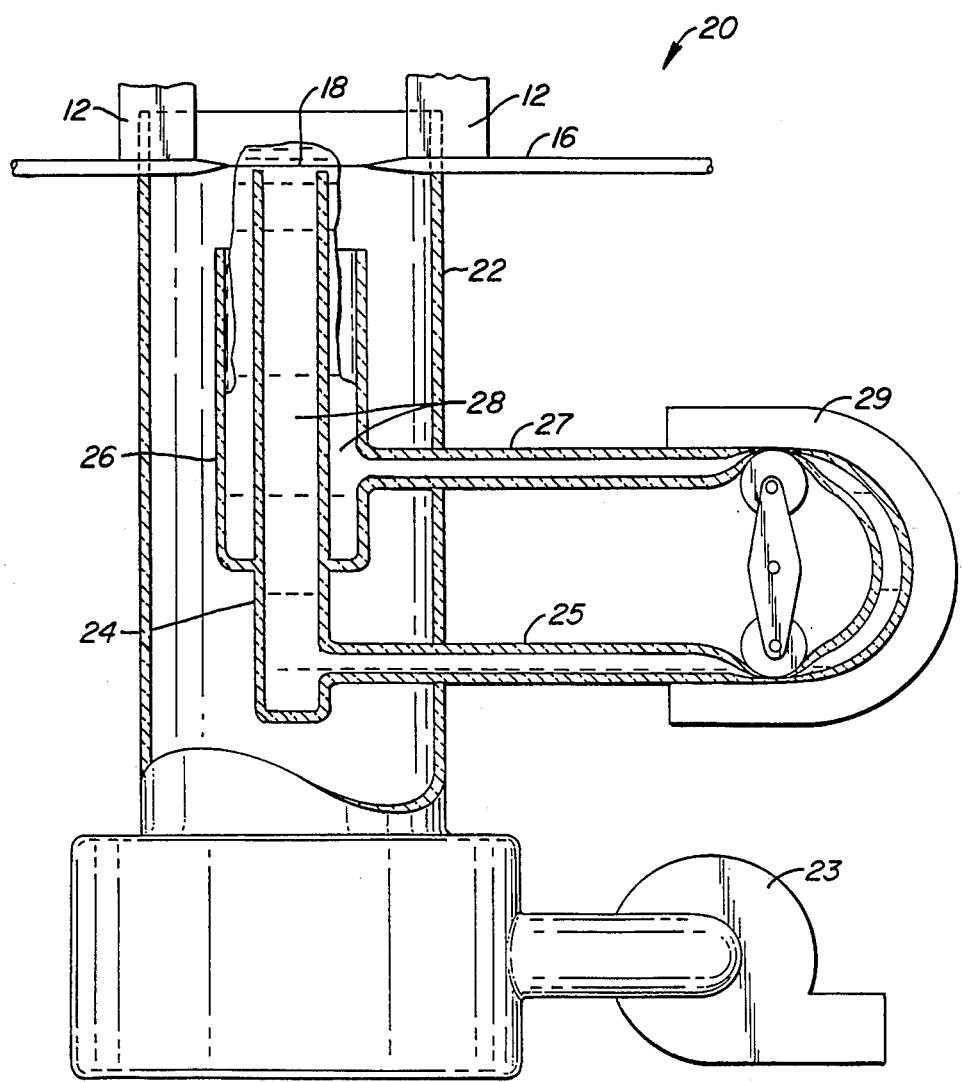
FIG._2.

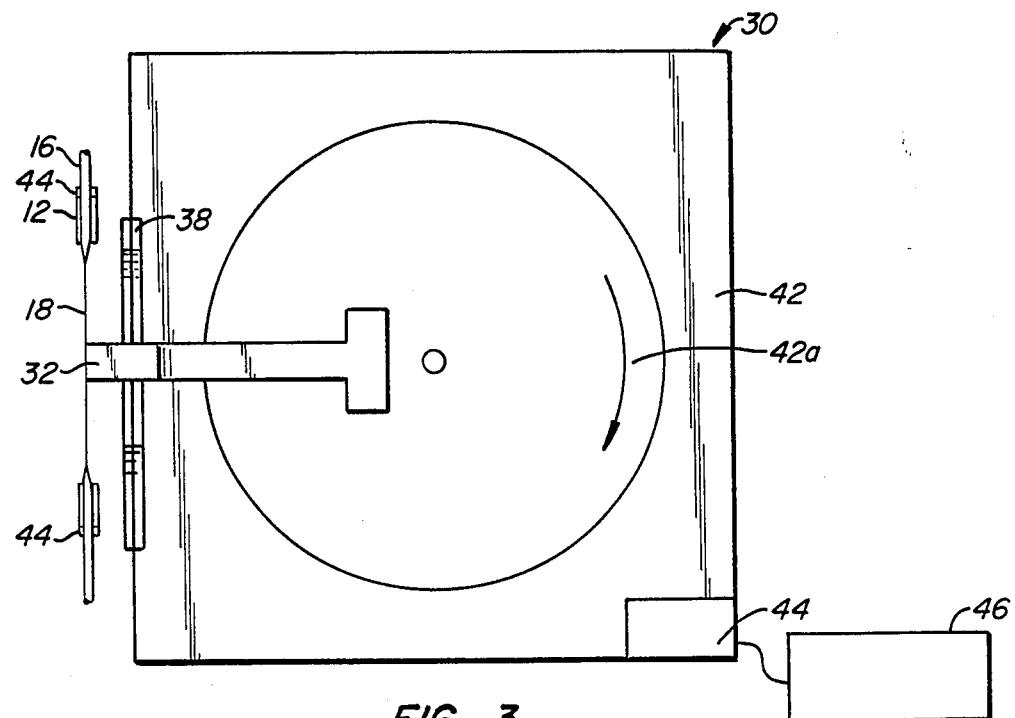
FIG._3.
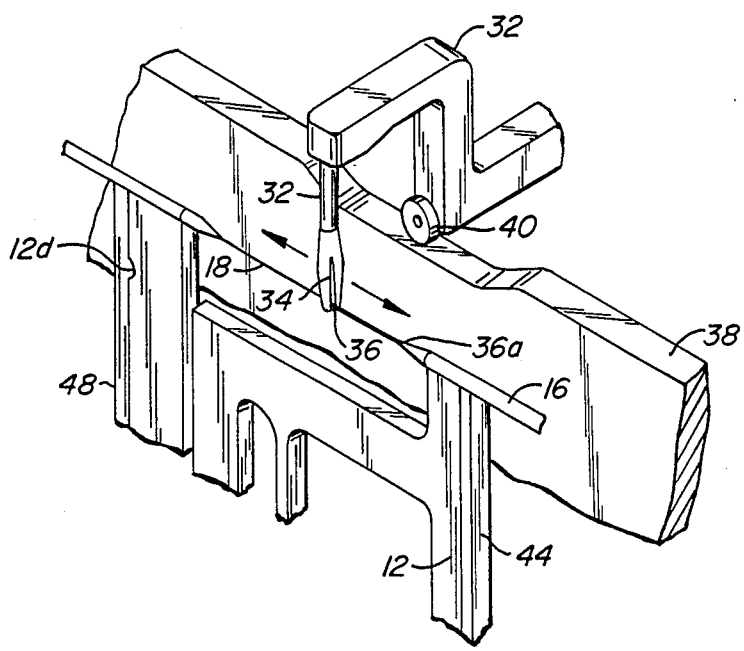
FIG._4.

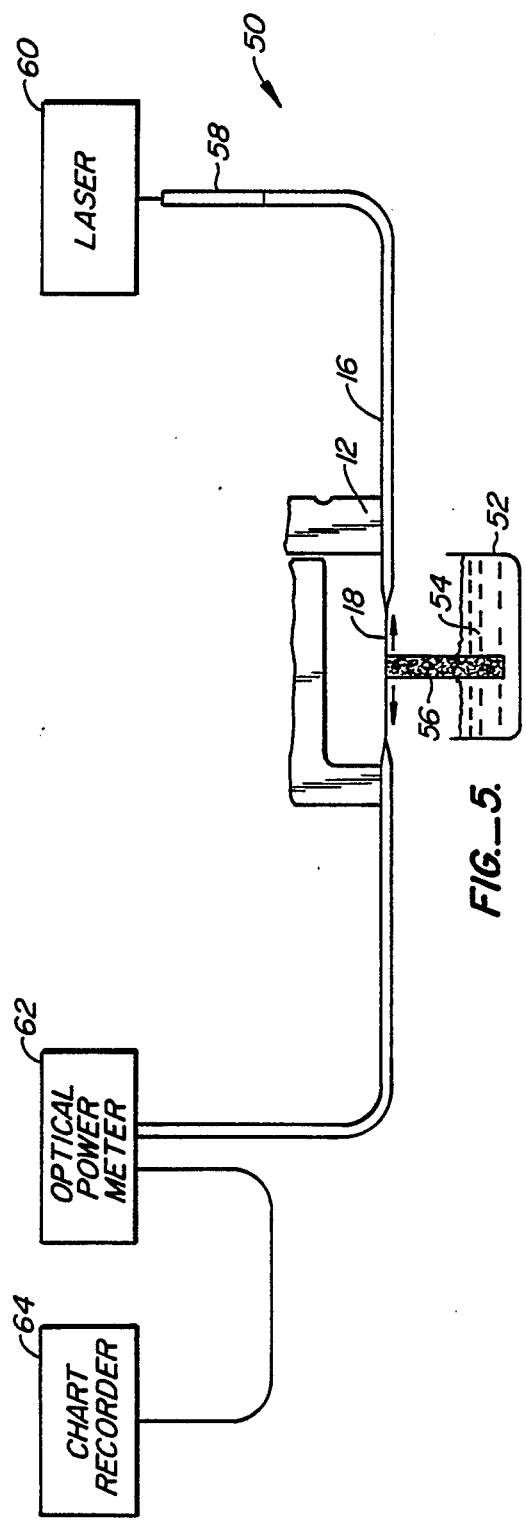
FIG._5.
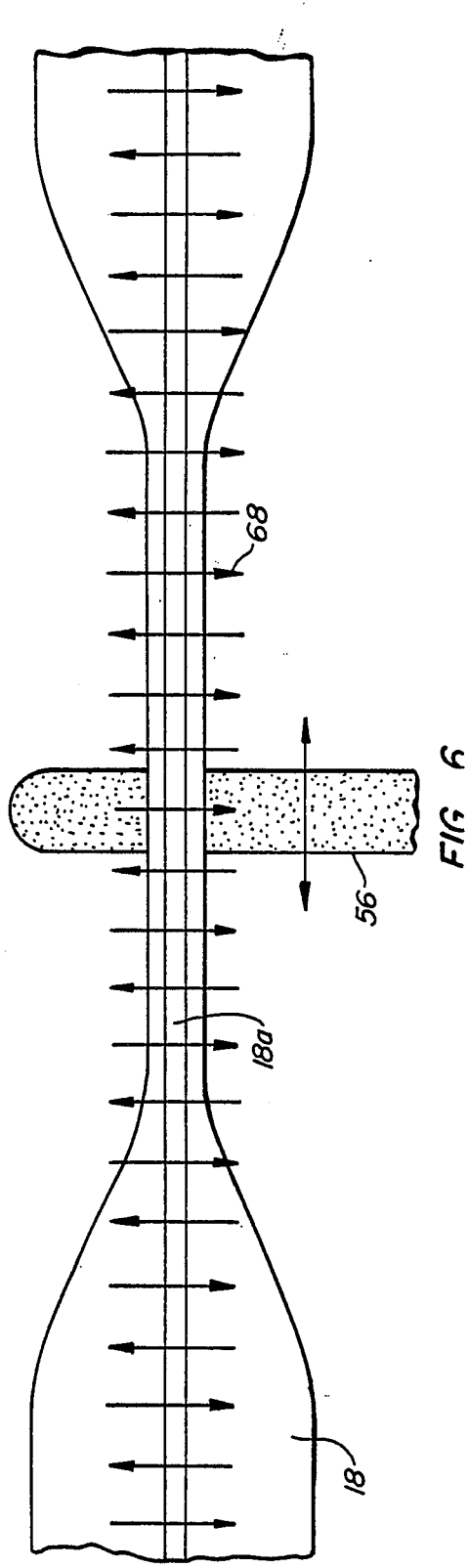
FIG. 6

PROCESS AND APPARATUS FOR MEASURING AN EVANESCENT FIELD IN AN OPTICAL FIELD

CROSS REFERENCE TO RELATED APPLICATIONS

"A Process of Fabricating a Portion of an Optical Fiber Capable of Reflecting Predetermined Wavelength Bands of Light", by D. C. Schmadel, Jr., U.S. Ser. No. 546,608, filed Oct. 28, 1983; "A Ruggedized Grated Optical Fiber", by J. E. Goodman et al, U.S. Ser. No. 546,609, filed Oct. 28, 1983; "Process of Tuning a Grated Optical Fiber and the Tuned Optical Fiber", by D. C. Schmadel, Jr. et al, U.S. Ser. No. 546,610, filed Oct. 28, 1983; "Optical Fiber Coating Apparatus", by J. E. Goodman, U.S. Ser. No. 546,617, filed Oct. 28, 1983; "Etching Fountain, by J. E. Goodman, U.S. Ser. No. 546,618, filed Oct. 28, 1983; and "Optical Fiber Holder", by J. E. Goodman, U.S. Ser. No. 546,619, filed Oct. 28, 1983.

This invention relates to optical fibers. More specifically, this invention relates to a process of fabricating a portion of an optical fiber to reflect predetermined wavelength bands of light.

BACKGROUND OF THE INVENTION

In a gaseous medium such as air, gratings and mirrors are used to control the direction and intensity of light. Light can also pass through a solid medium such as an optical fiber. It would be highly desirable to have a process of producing the effects of mirrors and gratings in the optical fiber. One of the methods of producing the grating in the fiber was described by B. S. Kawasaki et al in *Optics Letters*, Vol. 3, No. 2, pages 66–68 (August 1978). However, the Kawasaki et al paper was only applicable to gratings in fibers which have a photosensitive core material and with a reflectivity, r, of about 0.6, and having a long interaction length of about 50 centimeters. "Reflectivity" is defined as $r^2/i^2$, where r is the peak amplitude of the electric field for light which was reflected within the core and i is the peak amplitude of the electric field which is within the core and incident on the grating. "Interaction length" is defined as that length measured along the fiber axis over which both the grating and the incident light extend. A long interaction length causes the reflectance band to be very narrow spectrally. This limits the useful applications of the grating. Therefore, it would be highly desirable to have a process of forming gratings in an optical fiber which can exhibit long or short interaction lengths with either high, i.e, $r > 90\%$, or low reflectivities.

SUMMARY OF THE INVENTION

This invention is directed to an apparatus and process for determining the strength of the exposed evanescent field in an optical fiber. The apparatus and process are usefully incorporated into a process of forming gratings in optical fibers. The process permits a determination of the strength of the evanescent field at the surface of an optical fiber before, during and after etching and prior to the formation of gratings in the optical fiber which reflect predetermined wavelength bands of light. The process permits the fabrication of gratings which expose a predetermined strength of evanescent field. The apparatus can also test the optical fiber after the formation of the gratings. The process involves contacting a portion of an optical fiber wherein evanescent waves are encountered with a material having a higher index of refraction than that portion of the optical fiber while injecting into the optical fiber. The amount of light which is coupled out of the fiber through the high index of refraction material is a direct function of the evanescent field strength at the cladding surface of the optical fiber. The lost light does not reach a detector which can be placed on the end of the optical fiber opposite to the end in which light is injected. The loss can be recorded and correlated to determine the extent of etching of the optical fiber by a comparison with optical fibers which have been etched to a greater or lesser degree.

BRIEF DESCRIPTION OF THE DRAWINGS

FIG. 1 illustrates a holder for the optical fiber cable during processing.

FIG. 2 illustrates a cut-away view of an etching fountain.

FIGS. 3 and 4 illustrate an optical fiber coating apparatus.

FIGS. 5 and 6 illustrate an apparatus for testing an evanescent field in an optical fiber.

DETAILED DESCRIPTION OF THE INVENTION

An optical fiber contains a cental core through which the light travels surrounded by a cladding of a material having a lower index of reflection than the core. Usually, a protective jacket surrounds the cladding material. A suitable example of an optical fiber is a single mode light polarization maintaining fiber of the Andrew Corporation. To gain access to the cladding and core, the protective jacket is removed with a suitable stripping material such as Photoresist Remover 1112A, a product of the Shipley Corporation. The fiber is contacted with the photoresist remover for a sufficient time to remove the protective jacket. Elevated temperatures of about 50° C.–70° C. speed the reaction. At 60° C., the protective jacket is removed in about 5 to 10 minutes.

Removing the protective jacket exposes an optical fiber coated with a layer of indium. The indium material is supposed to hermetically seal the fiber. The exposed indium-coated fiber is fixed to a suitable holder of the additional processing steps of my invention. Preferably, the holder is fabricated from a corrosion-resistant temperature suitable material such as a ferronickel like Invar ® [36% nickel and 64% steel (a carbon content of 0.2%)], or other suitable metals or materials. A method of fixing the indium exposed portion of the fiber is with solder, such as indium solder. Of course, if the fiber does not have an indium coating, then an appropriate material capable of attaching the holder to the fiber should be used. Any holder is suitable provided that the tension on the fiber can be adjusted and it also allows complete access to the exposed portion of the fiber. Initially, the tension is adjusted to maintain a positive tension on the optical fiber.

A preferred holder and optical fiber unit is illustrated as 10 in FIG. 1. Although used in this process with optical fibers, the holder is also suitable for use in processes which involve fine wires, rods, and the like, having diameters on the order of from about 5 to 100 micrometers. The holder 12 is fabricated from Invar ® or other suitable temperature-stable materials. Preferably, the holder 12 is a unitary piece with the exception of adjusting means 14. The optical fiber 16 is fixed to the holder 12 with indium solder or by other suitable means. The holder 12 allows complete access to the exposed indium-coated portion to the optical fiber 18 for subsequent processing. The holder 12 has sections 12a and 12b which are thiner than the thickness of the holder 12. This design provides a means for the movement of the holder 12 to tension the fiber 18 by the action of adjusting means 14 on the lever arm portion 12c of the holder 12 without twisting, i.e., moving out of a fixed plane. For example, if the holder is about 4.7 mm thick, then 12a and 12b should be about 1.1 mm across. In other words, 12a, 12b, 12c and 14 act as a tensioning means for the fiber 18 while maintaining it in a fixed plane during tensioning. A suitable adjusting means 14 is a screw of Invar ® or stainless steel. An adjustment of about 0.5 mm is suitable for tensioning the fixed optical fiber section 18. Optionally, the holder 12 incorporates a means for attaching 12d, the holder 12 to subsequent processing apparatus as disclosed, for example, in FIGS. 3 and 4. More specifically, the notch 12d orients the holder 12 and permits it to be attached to further processing apparatus in a reproducible and accurate fashion. Suitable dimensions for the holder 12 are about 50 mm from edge to edge across the top of the holder where the fiber 16 is connected (i.e., width) and about 43 mm for the length perpendicular to the width.

After the fiber is mounted in the holder, it is then placed into suitable etching apparatus which contains a suitable indium etchant solution such as 1 molar ferric chloride to remove the indium. A suitable etching period is from about 3 to 10 minutes at room temperature. Alternatively, any commercially available copper printed circuit board etchants, available from the Shipley Corporation, are also suitable. Any etching apparatus is suitable provided that it exposes only the fiber and not the holder to the etching material.

A preferred etching apparatus is the etching fountain 20 illustrated in FIG. 2. The fountain 20 is preferred because it can be used with harsh and dangerous chemicals, such as ferric chloride without a hood to vent the fumes. The fountain 20 has an outer jacket 22 connected to a means for creating a downward flow of air such as a pump 23. The pump 23 creates a downward air flow and removes the noxious vapors and gases from the air space over the work piece. Inside the outer jacket 22 is a central inner chamber 24 connected to a means for injecting a fluid into the chamber 24 such as a tube 25. The tube 25 is connected to a means for circulating a fluid such as pump 29. Surrounding the inner chamber 24 is a an outer overflow receptacle 26 which is also connected to a means for removing fluid from the overflow receptacle 26 such as a tube 27. The tube 27 is also connected to the pump 29. The pump 29 circulates an etchant fluid or solution 28. The upper part of the outer jacket 22 has a means for holding a work piece such as a slit. The slit fits the optical fiber holder 12 and situates the optical fiber 18 or other work piece such as a fine wire or rod just above the top of the inner chamber 24. The inner chamber 24 is designed so that the pumping action of pump 29 exposes the indium coated portion of the fiber 18 to the solution 28 but not the outer jacketed portion of the fiber 16. This prevents the solution from being contaminated by the outer jacket 16. For the indium etching, the pump 29 should deliver a uniform flow so that the indium layer is evenly removed. However, in the next step, when the inner cladding is removed with a suitable cladding etching to a depth wherein evanescent waves are encountered, the pump 29 should create an oscillating head of etchant solution so that the cladding ends taper to the exposed center without sharp light leaking transitions. The taper is illustrated in FIG. 6. Of course, the etchant solution should not oscillate so violently that it is contaminated by the indium coating, i.e., this second etchant solution should only touch the cladding where the previous etching has removed the indium coating. A peristaltic pump 29, as illustrated, is preferred for this application. Of course, 25 must be flexible when 29 is a peristaltic pump. A suitable material is Tygon ® tubing. Since the etchants only touch the fiber 18, the holder 12 may be but does not have to be constructed out of materials which are inert to the etchant solutions. The pump 23 keeps any noxious fumes away from the holder 12 and people working in the area. Although the etching fountain 20 is illustrated for one fiber, it can be scaled up to accommodate any number of fibers, wires or rods. With one fiber, 22, 24, and 26 are preferably tubular in shape, while in a more-than-one fiber design, 22, 24 and 26 are preferably rectangular in shape.

When the indium has been removed, the holder and fiber are removed from the fountain and rinsed in water, and then placed into a second etching fountain to etch away the outer cladding of the optical fiber to a depth wherein evanescent waves are encountered. A suitable etchant solution is four parts of an ammonium bifluoride mixture with water and one part hydrofluoric acid with water, such as "BOE etchant (5-1)" available from Allied Chemical Corporation in Morristown, N.J. A suitable etching period is from about 3 to 8 hours. With the Andrew Corporation fiber, the core and cladding will have a diameter of about 66 micrometers before etching and about 6–10 micrometers after etching. The fountain is designed, as discussed above, to expose only that portion of the fiber from which the indium had been removed. The fountain is operated with a pulsating or oscillating flow pattern to produce a fiber with a taper as illustrated in FIG. 6.

When the fiber has been sufficiently etched, which in the case of the Andrew Corporation fiber might be to a total diameter of about 6 micrometers to about 12 micrometers and preferably about 8 to about 10 micrometers, the fiber and holder are removed from the second etching fountain, rinsed and then placed in a primer coating apparatus. An example of a suitable primer is C-55, HMDS primer, a product of the Shipley Corporation. The priming takes from about 10 to 20 seconds. Any priming apparatus is suitable provided that it primes only the etched portions of the fiber. Preferably, the priming is done by vapor deposition. Alternatively, the coating apparatus described hereinafter can be employed. The holder, the indium coating and other extraneous materials should not contaminate the primer material.

A preferred coating apparatus 30 is illustrated in FIG. 3 with a more detailed section of the apparatus illustrated in FIG. 4. The apparatus 30 has a control arm 32 which incorporates a fluid applicator head 34 for photoresist primer or photoresist and the like. A suitable applicator head 34 is a ruling pen nib. The surface tension of the fluid 36 which is to coat the object such as primer and/or photoresist holds it between the two nib halves which define the fluid reservoir until it is applied to the fiber 18. The control arm 32 is connected to a reversibly rotating disc 42a mounted on a base 42. A control switch 44 and power 46 provides the means for reversibly rotating the control arm 32 in a reciprocating fashion. A guide wheel 40, such as a wheel or bearing, is attached to the lower portion of the control arm 32 as it traces a pattern back and forth across a control track 38 having two upper portions and a lower portion therebetween. Generally, the lower portion of the control track 38 is configured so that about 5 to 25 millimeters of the fiber are coated. Of course, it can be configured to coat any length. When the wheel 40 is in the lower portion of the track 38, the nib 34 containing the material 36 to be coated on the fiber 18 straddles the fiber 18 while material 36 is deposited on the fiber 18 as coating 36a. The thickness of the coating 36a is a function of the viscosity of material 36 in the nib 34 and the speed at which control nib 34 travels across the optical fiber. The track 38 is configured so that the material 36a only coats the etched portion of the fiber 18. The fiber is held by holder 12 and positioning means 48 in the coating apparatus 30. The holder 12 is situated such that the object to be coated is within the nib halves as the control wheel is in the lower portion of the control track 38. Preferably, the lower portion of the track is configured so that the nib halves never touch the fiber 18. The attaching and centering means 12d in holder 12 ensures that the fibers 16 and 18 are held in the same position. The positioning means 48 is designed to surround and support the outside of holder 12 but leave the surface holding the fiber 16 open for coating by the nib 32. The control switch 44 can be a manual switch which the operator merely reversed or an automatic switch to reverse the direction of the arm 32 after it makes a pass over the fiber 18 and rises to an upper portion of the control track 38. The drive for disc 42a can be any standard gear or belt drive. The drive mechanism, not illustrated, is incorporated into the control switch unit 44. Alternatively and not illustrated, the control arm can have a drive motor and guide track, as opposed to the rotating disc, that will permit it to run parallel with the fiber 18 and the control track 38. This apparatus is preferred because it overcomes the surface tension problems of applying a fluid such as photoresist to a thin object, such as a wire, rod, optical fiber, and the like, wherein the diameter is on the order of about 5 to 50 micrometers and more usually on the order of about 10 micrometers for an optical fiber.

After priming, the holder and fiber are removed from the priming apparatus and placed in a photoresist coating apparatus. The photoresist coating apparatus applies a positive photoresist such as Microposit 1400-27 ® or Microposit 1400-33 ®, products of the Shipley Corporation. Any photoresist coating apparatus is suitable provided that it applies photoresist only to that portion of the fiber which has been primed. A preferred apparatus is illustrated in FIGS. 3 and 4 and was described above. The photoresist is not applied to those portions of the fiber still coated with indium, nor is the photoresist ever in contact with the holder. This eliminates the possibility of contamination of the photoresist coating. The coating operation as well as all following operations may be implemented in an amber light environment to avoid unwanted exposure of the photoresist. The amber light source should preferably allow less than about 3 millijoules/cm$^2$ of light between 350 nanometers (nm) and 480 nm wavelength to fall on the photoresist surface.

Thereafer, the fiber and holder are removed from the photoresist coating apparatus and the adjustable holder is adjusted so that the fiber is loose. If during the baking procedure the dimensions of the holder or fiber should change slightly, the fiber will not be stressed to the point of breaking.

Optionally, the fiber and holder are then placed into an oven for a soft bake. For example, with Microposit 1400-27 ® or Microposit 1400-33 ®, the soft bake consists of heating the fiber and holder in an oven for about 20 to about 40 minutes and preferably 30 minutes at about 90° C. After the soft bake, the fiber and holder are placed in a container to avoid exposure to cooler, ambient air, removed from the oven, and allowed to cool slowly. Thereafter, the fiber and holder are removed from the container and the adjustable holder is readjusted so that the fiber is taut.

The fiber and holder are then placed in an exposure apparatus in which they are exposed to interfering beams from a light source such as krypton laser, Model 3000-K produced by Coherent, Inc. The particular laser and wavelength of light is selected to match the exposure sensitivity of the photoresist. A wavelength of about 413 nm is ideal for Microposit 1400-27 ® or Microposit 1400-33 ®. The exposure of the photoresist to interfering beams of light creates a pattern wherein the photoresit is exposed periodically along the fiber for a spatial separation of exposure peaks or lines of about 0.3 micrometers. Preferably, the exposure peaks each lie in a plane perpendicular to the fiber axis. The light from the laser is spatially filtered by means of a pinhole and then expanded and collimated. The exposure time is from about 1 to about 5 seconds for a 2-inch diameter beam of about 400 milliwatts total power. When varying the grating dimensions, a determination is made as to the desired grating size and an interference angle and a light source is selected which can create such a pattern. Thereafter, a suitable photoresist is selected which is sensitive to light of that wavelength.

After exposure, the fiber and holder are removed from the exposing apparatus and the holder is readjusted so that the fiber is loose. Thus, if the developer should be at a slightly different temperature thereby cooling portions of the holder, it will not subject the fiber to additional stress which might cause it to break.

Thereafter, the fiber and holder are placed into a developing apparatus. The developing apparatus is a fountain which contains a suitable developer for the photoresist such as Developer No. 35 CD 23, a product of the Shipley Corporation. The fiber is exposed to the developer for from about 15 to 60 seconds, and preferably about 30 seconds, at room temperature. The developing apparatus is designed to expose the developer to only those portions of the fiber which are coated with photoresist. Thus, the developer will not be contaminated by, for example, the indium on the fiber or the holder. The fiber is then rinsed in deionized water or other suitable rinses. The rinsing can take place either in a large bath where the fiber and holder can be submerged or the fiber and holder can be washed in a fountain similar to the fountain used for the developer solution.

After the bath is washed, it can then undergo an optional flat exposure procedure at the same light intensity as the original exposure and for a period of from about 1 to 10 seconds. The flat exposure procedure consists of exposing the fiber and holder to white light or light which is within the absorbance band or the exposure band of the photoresist to expose those portions of the photoresist which remain on the fiber and have not been exposed by the original laser beam exposure.

The fiber and holder are placed in an ion beam etching apparatus.

The ion beam etching apparatus uses a source of reactive ions such as fluorine ions derived from tetrafluoromethane or other suitable sources, or other suitable ions to etch the fiber and the photoresist. The fluorine ions will etch that portion of the fiber which is not covered with the lines of the photoresist. Thus, the ion beam will etch gratings into the fiber. The etching takes from about 10 to 30 minutes. Generally, the gratings will be etched from about one-third of the way to about one-half of the way around the circumference of the optical fiber.

A preferred option requires that the fiber can be quickly etched in the ion beam apparatus prior to the chemical etch and the priming and photoresist coating to create a fiber with an off-center core where the cladding is thinner on one side. The thinner cladding area exposes more evanescent wave and orients the fiber for the grating formation in this thinner cladding section. The ion beam etcher need only remove about 1 to 2 micrometers from a side of the fiber to create the necessary offset to orient the fiber.

After the etching, the fiber and holder are removed from the ion beam etching apparatus and placed in a photoresist removal apparatus. The photoresist removal apparatus is again a fountain which allows the photoresist remover, such as Remover 1112A, a product of the Shipley Corporation, to remove the remaining photoresist on the etched fiber. The photoresist is exposed to the remover for from about 10 seconds to about 10 minutes. Alternatively, a solution of nine parts $H_2SO_4$ and one part 50% hydrogen peroxide at approximately 90° C. can be used as a remover. The fountain is designed so that only the portion of the fiber which contains photoresist is exposed to the photoresist remover. The finished fiber has a substantially uniform grating along its surface. The gratings on the fiber will reflect specific wavelengths of light passing through the fiber.

The amount of light the fiber reflects can be determined by adjusting the previous steps to create a fiber having a predetermined grating configuration. The closer the gratings are to the core, the greater the reflectivity of the gratings. Alternatively, the strength of the reflectance can be adjusted by adjusting the ion beam's etching time. The reflectivity or the amount of light the fiber will reflect is related to the depth of the grooves of the grating. The greater the depth, the greater the amount of the reflected light. Finally, the angle of interference of the exposing light and the exposing light wavelength determine the spacing of the gratings.

For example, a 0.3 micrometer grating peak spacing requires each of two interfering beams to have propagation vectors which have an angle of 96° between them, or lie nearly in the same plane which contains the axis of the fiber, and have a bisector of the angle between them which is or is nearly perpendicular to the fiber axis. Taking into account the refractive index of the fiber, a 0.3 micrometer grating spacing will reflect light having a wavelength of about 8300 Angstroms. The 0.3 micrometer spacing is peak to peak or valley to valley. The width of a peak or valley is about 0.15 micrometer and the depth from a peak to a valley is about 0.15 micrometer. The secnod of the interfering beams can be derived from the first beam through the use of a beam splitter. Alternatively, the interference pattern can be produced by the use of a mirror capable of producing Lipman fringes. The interference pattern is created by having the original beam interfere with itself.

If one wants to have a grating which will reflect a lower wavelength light, then the angle between the propagation vectors is adjusted to be more than 96°, for example 100° or 110°. A smaller angle causes the exposed pattern in the photoresist to have a lower spatial frequency. In other words, the separation between the exposed photoresist lines will be greater.

More specifically, varying the process parameters permits the fabrication of gratings with interaction lengths that vary from about 100 wavelengths to about 1 centimeter. The reflectivity r can be varied from about 0.05 to about 0.9 or higher. This wave reflectivity enables to fabrication of gratings that can be adjusted to reflect wavelengths of light between about 7000 Angstroms to about 20,000 Angstroms or higher. Changing the laser lights source can extend the range below 7000 Angstroms or about 20,000 Angstroms.

Furthermore, this process also allows one not only to change the spectral location of the light which is reflected by the grating but also change the shape of the wavelength band. For example, the fiber can be ion beam etched through shutters to reduce the exposure at the ends of the grating. This causes the strength of the reflectivity to vary along the gratings, i.e., the center of the grating portion would exhibit a strong reflectivity and the ends would exhibit weak reflectivity. One could use shutters which vary the amount of the ion beam to etch the grating so as to make gratings which might have a gaussian dependency. Such an adjustment in the process permits the fabrication of gratings which have suppressed side lobes.

Optionally, the etching process can be monitored by the following process to determine the amount and effect of cladding etching so as to better control the reflectivity of a grating. This process occurs during the etching chemical procedure and prior to actually forming the grating on the fiber. The monitoring process requires interrupting the etching chemical process, removing any etchant solution from the fiber, injecting light of nearly the wavelength of the desired reflectance band into an end of the fiber, contacting the etched fiber with a wick saturated with a liquid having an index of refraction higher than that of the fiber core material, for example, phenol, methyl salicylate (i.e., oil of wintergreen) and the like, and measuring the decrease in light output from the fiber end opposite the injection end as caused by the placement of the wick. The accuracy of the process is partly dependent upon knowing which size and contacting length on the fiber touched by the wick. This wick loss decrease, in light output, relates to the strength of the exposed evanescent waves. The greater the light loss, the more the evanescent waves are exposed.

FIGS. 5 and 6 illustrate an apparatus 50 for measuring the evanescent field in an etched optical fiber 18. The optical fiber 16 and the etched portion 18 thereof are held in a holder 12. The core of the etched optical fiber 18 is indicated as 18a. A container 52 holds a solution 54 having a higher index of refraction than the etched optical fiber 18 in the holder 12. Suitable materials are phenol, methyl salicylate, and the like. A stable wick 56, fabricated from a material such as a urethane foam polishing cloth, is placed in the solution 54. Preferably, the wick should be at least as thick as the fiber 18, have known width, and not be subject to expansion. Since the etched length of the fiber is usually about 1 to 4 cm, a suitable width is from about 0.02 mm to about 0.1 mm and preferably is about 0.05 mm. Preferably, the wick should wet the same length of the fiber as the width of the wick because the accuracy is partly based upon knowing the length of the fiber exposed to the high index of refraction solution. To test the entire length of the etched fiber 18, either the wick 56 must be movable along the fiber 18 or the fiber 18 and holder 12 must be movable along the wick. This movement can be accomplished by a motor or person physically moving the fiber or the wick.

With the wetted wick 56 touching the fiber 18, one end of the fiber contains a holder system 58 capable of permitting light from a laser 60 to be injected into the fiber 16. Any standard holder and lense focusing system capable of putting the laser light within the angle of acceptance of the fiber is suitable. The laser should be selected to emit light having a wavelength of interest for reflection when the gratings are formed. For example, if the gratings are to be designed to reflect light at about 8300 Angstroms, then the laser can be a GaAs laser that emits light having a wavelength of about 8300 Angstroms. The light passing through the fiber 16 containing the cladding and core unit 18 is monitored on an optical power meter 62. Any suitable optical power meter can be used or a photodiode capable of converting the optical light signal into an electrical signal can be used. The signal obtained from the optical power meter 62 is recorded on a recorder 64 such as a chart recorder.

As illustrated in FIG. 6, given a constant evanescent field, the greater the depth of the etching, the larger will be the wick light loss coupled out of the fiber 18 through the wick 56 containing the high index of refraction material 54 and the lower will be the recording on the chart recorder 64. By moving either the fiber 18 or the wick 56 along the etched portion of the fiber 16, the uniformity and depth of etching can be determined. Since the gratings will be formed within the fiber 18, the field will be at least as strong as the field exposed during the test. This process gives a representative correlation between the strength of the exposed field after grating formation.

By repeating this monitoring process several times during the etching process, the process also provides a method of monitoring the etch rate of the fiber. By etching many fibers to have different wick losses and then forming gratings and measuring the reflectivity, the relationship between wick loss for a known length of fiber and reflectivity for a finished grating can be determined empirically for a particular manufacturer's fiber. Using this relationship, the reflectivity of a grating or grating portion can be approximately established immediately after the cladding etching and before the grating formation.

The invention has been described with respect to preferred embodiments. However, it should be understood that the invention is not intended to be limited in any way of the preferred embodiments. Modifications which would be obvious to the ordinary skilled artisan are contemplated to be within the scope of the invention.

What is claimed is:

1. An apparatus for measuring the exposed evanescent field in an optical fiber comprising:
   a light source;
   means for injecting the light from said source into an optical fiber;
   an optical fiber connected at a first end to said means for injecting the light;
   a wick for contacting a portion of the cladding of said optial fiber with a material having a higher index of refraction than said cladding, said wick having a known contacting length on the fiber touched by the wick; and
   means for measuring the intensity of the light emitted from the end of said optical fiber opposite to said end into which said light is injected; and
   means for moving said wick along said fiber.

2. The apparatus according to claim 1 wherein said wick moves along said cladding.

3. The apparatus according to claim 2 which further comprises means for recording said measured intensity of said light.

4. The apparatus according to claim 3 which further comprises an optical fiber holder to position said cladding at said wick.

5. The apparatus according to claim 4 wherein said wick has a width along said optical fiber of from about 0.02 to about 0.10 mm and said cladding has a diameter of from about 5 to about 50 micrometers.

6. The apparatus according to claim 5 wherein said higher index of refraction material is selected from the group consisting of phenol or methyl salicylate.

7. The apparatus according to claim 6 wherein said wick is fabricated from a urethane foam.

8. The apparatus according to claim 7 wherein said light source is a light-emitting diode or a laser.

9. An optical fiber evanescent field measuring kit having component parts capable of being assembled in conjunction with an optical fiber, said optical fiber having at least a portion of an exposed cladding surrounding a core, the kit comprising:
   a light source;
   a holder capable of fitting on an end of said optical fiber and injecting light from said source into said optical fiber;
   an optical power meter capable of measuring light emitted from the opposite end of said fiber from which said light was injected;
   a wick, said wick capable of incorporating therein a material having a higher index of refraction than said cladding; and
   a means for moving said wick along said fiber.

10. The kit according to claim 9 which further comprises a sufficient quantity of said higher index of refraction material to wet said wick.

11. The kit according to claim 10 which further comprises a chart recorder to record the measured output from said optical power meter.

12. A process of measuring exposed evanescent field in an optical fiber comprising:
   injecting light into an end of an optical fiber, said optical fiber having a cladding surrounding a central core;
   measuring the output from an end opposite to said injection end;
   contacting a portion of said cladding with a material having a higher index of refraction than said cladding; and
   moving said material along said fiber.

13. The process according to claim 12 further comprising etching a portion of said cladding.

14. The process according to claim 13 further comprising recording the output from said measuring of said output from said end opposite to said injection end.

15. The process according to claim 14 wherein the injected light is coherent light.

16. The process according to claim 12 wherein said optical fiber is a single-mode or multi-mode optical fiber.

17. An apparatus for measuring the exposed evanescent filed in an optical fiber comprising:
 a light source;
 means for injecting the light from said source into an optical fiber;
 an optical fiber connected at a first end to said means for injecting the light;
 a wick for contacting a portion of the cladding of said optical fiber with a material having a higher index of refraction than said cladding;
 means for measuring the intensity of the light emitted from the end of said optical fiber opposite to said end into which said light is injected; and
 means for moving said wick on said fiber relative to each other.

18. A process of measuring the exposed evanescent field in an etched optical fiber comprising:
 injecting light into an end of an optical fiber, said optical fiber having a cladding surrounding a central core;
 measuring the output from an opposite end to said injection end;
 contacting a portion of said cladding with a material having a higher index of refraction than said cladding; and
 moving the contacting step along different parts of said cladding.

* * * * *